(12) United States Patent
Shi (10) Patent No.: US 8,021,382 B2
(45) Date of Patent: Sep. 20, 2011

(54) SAFETY SINGLE USE BLOOD LANCET DEVICE WITH ADJUSTABLE PUNCTURE DEPTH

(75) Inventor: Guoping Shi, Suzhou (CN)

(73) Assignee: Pengfei GU, Suzhou (CN)

( * ) Notice: Subject to any disclaimer, the term of this patent is extended or adjusted under 35 U.S.C. 154(b) by 679 days.

(21) Appl. No.: 11/649,246

(22) Filed: Jan. 4, 2007

(65) Prior Publication Data

US 2008/0039886 A1 Feb. 14, 2008

(30) Foreign Application Priority Data

Aug. 14, 2006 (CN) .................. 2006 2 0077771 U (51) Int. Cl.
*A61B 17/32* (2006.01)

(52) U.S. Cl. ....................................... 606/182

(58) Field of Classification Search ............ 606/181, 606/182

See application file for complete search history.

(56) References Cited

U.S. PATENT DOCUMENTS 6,852,119 B1 * 2/2005 Abulhaj et al. ............. 606/182
2003/0088261 A1 * 5/2003 Schraga ..................... 606/182

FOREIGN PATENT DOCUMENTS

| CN | 01244815 | 3/2002 |
| CN | 01263172.8 | 6/2002 |
| CN | 02286472.5 | 10/2003 |

* cited by examiner

Primary Examiner — S. Thomas Hughes
Assistant Examiner — Julie A Szpira
(74) Attorney, Agent, or Firm — Oliff & Berridge, PLC (57) ABSTRACT

A safety single use blood taking lancet, having an adjustable puncture depth, includes a blast-off structure and an adjusting head. The blast-off structure comprises a sleeve, an end cap, a needle core with a needle pin, a spring and a push element. Two elastic clips extend from the end cap. The needle core and the elastic clips form a lock structure and a structure blocking the needle core to return to an initial position. An inside face has a revolving inclined plane or a revolving ladder plane. When changing the revolving angle of the adjusting head, the revolving inclined plane or the revolving ladder plane bumps into an impact face of the needle core at different depth of the needle hole.

10 Claims, 6 Drawing Sheets

SAFETY SINGLE USE BLOOD LANCET DEVICE WITH ADJUSTABLE PUNCTURE DEPTH

BACKGROUND

The present utility model relates to medical blood taking instrument, especially to a safety single use blood taking lancet having a puncture depth that is adjustable. The depth of puncturing into the skin of a human being of this blood taking lancet can be adjusted, so as to adapt to different ages and different kinds of skin layer.

Compared with the general single use safety automatic blood taking lancet, the safety single use automatic blood taking lancet with adjusting head has great advantage in the control of the puncture depth. It changes the previous disadvantage that the blood taking puncture depth could not be changed, in that it can change its puncture depth according to different blood taking objects, such as, for example, adult or children, and male or female, etc., thus can achieve better blood taking effect. In practice, doctors and nurses have given positive review of such products. Also, patients who have had their blood taken welcome these products.

In prior art, there are many kinds of blood taking needles with adjustable puncture depth. Several patent applications relating to adjustable puncture depth have been disclosed in Chinese patents. Among these patents, the following three applications are most related:

1. an utility model named "Adjusting head of blood taking puncture depth", 01244815.X, filed on Jul. 13, 2001.
2. an utility model named "Improved adjusting head of blood taking puncture depth", 01263172.8, filed on Oct. 9, 2001.
3. an utility model named "improved safety one-off adjustable blood taking needle", filed on Nov. 29, 2002.

In the above-mentioned three applications, although they disclosed different adjusting structures, the basic theory is using a screw structure to move out the end face of the needle hole in the corresponding position of the axis, thus adjusting the extended length of the needle. Although this structure has beneficial effect in past practice, it has the following disadvantages: 1) when moving, the adjusting head would move back and forth relative to the shell body. Therefore, there is larger error between the actual regulated quantity and the academic regulated quantity, which leads to decreased precision of the adjustment of the puncture depth; 2) the regulated quantity of each kind is hard to reach an identity; 3) the adjusting head and the shell body connected by the screw structure, which is very complex. Thus, it is very hard to guarantee that the move precision and the product quality of every two components are the same; and 4) the arrangement of the screw structure would increase the volume and the length of the blood taking needle.

On the other hand, as a complete automatic blood taking apparatus, the design of the blast-off structure is very important, because this structure not only relates to the problem of safety and convenience. It also relates to the volume, cost and reliability, and other issues of the blood taking needle. As a product to be introduced to the market, attention should be paid not only to the effect of adjusting head and the effect of blast-off structure, but also to the integrate performance and reliability of the combination of the adjusting head and blast-off structure, thus to make the best optimized overall effect.

SUMMARY

One objective of the disclosed embodiment is to provide a safety single use or disposable blood taking lancet or blood sampling needle, which has a puncture depth that is adjustable, which is structurally reliable, functionally reliable, easy to handle and use, and performance stable.

In order to achieve the above-mentioned objective, the following technical solution may be adapted: a safety single use blood taking lancet with a puncture depth that is adjustable, including a needle core blast-off or release structure and an adjusting head with adjustable puncture depth, characterized in that:

the needle core blast-off structure comprising:

a sleeve and an end cap composing a cylinder-type outer shell, two elastic clips inside the sleeve extending from the end cap, pothooks being mounted symmetrically inward the end of the two elastic clips, the other end of the sleeve being an opening;

a needle core with needle tip mounted between the two elastic clips, side ears or hook engagement elements being mounted on the needle core corresponding to the pothooks, the side ears and the pothooks cooperating to form the needle core locking structure; the distance between the two pothooks on the two elastic clips being less than the side extending width of the two side ears under free state, and a block off face or blocking face being mounted at the top of the side ears; after injection, a structure which blocks the needle core from returning to its initial or original position being formed between the blocking face and the pothooks so as to form a single use injection structure; two slip guide plates being symmetrically mounted at two sides of the needle core;

an injection spring mounted between the end of the needle core and the end cap, and being biased toward the direction of injection;

a push element mounted slidably in the opening of the other side of the sleeve, whose front side extending from the opening, the central axis being along the injection trace; a push element inclined plane or cone plane structure, which makes the push element to separate from the two sides, being mounted at the end of the push element corresponding to the two elastic clips, the inclined plane and the end of the two elastic clips composing a blast-off structure; a sliding chute being mounted in the inwall or inner wall of the injection trace of the push element, which corresponds to the guide plates, the guide plates and the sliding chute cooperating to form the injection guide structure; when viewed from above, the guide structure and the lock structure appearing as a square crossing;

the adjusting head being mounted in the head end of the push element, which connects to the push element rotatably; an outside face for contacting the skin of an injection target, such as a human being, being mounted at the front of the adjusting head, a needle hole being arranged in the centre of the outside face, an inside face being mounted in the back end of the needle hole, which faces directly to the needle core, said inside face being a revolving inclined plane or revolving ladder plane, an impact face being mounted in the head end of the needle core, which corresponds to the revolving inclined plane or the revolving ladder plane, when changing the revolving angel of the adjusting head, the revolving inclined plane or the revolving ladder plane bumping into the impact face of the needle core at different depth of the needle hole.

The reference numbers in the above-mentioned drawings are: 1. end cap, 2. spring, 3. needle core, 4. push element, 5. sleeve, 6. adjusting head, 7. nut cap, 8. elastic clip, 9. pothook, 10. side ear (or hook engagement element), 11. inclined plane, 12. guide plate, 13. sliding chute, 14. block off face (or blocking face), 15. outside face, 16. needle hole, 17. revolving inclined plane, 18. revolving ladder plane, 19. impact face, 20. locating slot, 21. heave, 22. projection, 23. spacing flat slot (or spacing slot), 24. detecting pole, 25. axis neck, 26. fixed slot (or fixing slot), 27. barb tool, 28. claw tool.

DETAILED DESCRIPTION OF EMBODIMENTS

Figure 1:
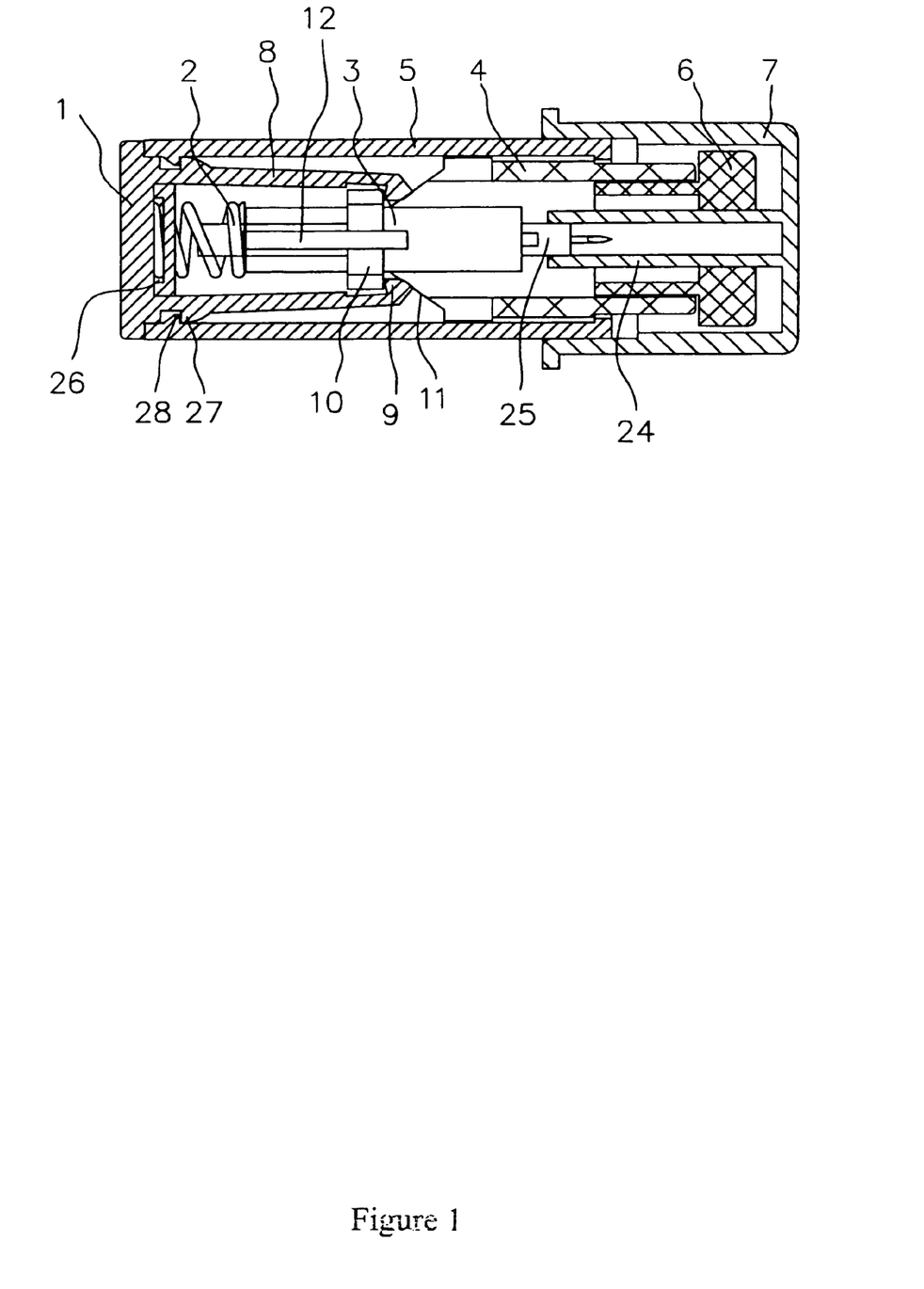
FIG. 1 is a structure view of an embodiment.
Figure 2:
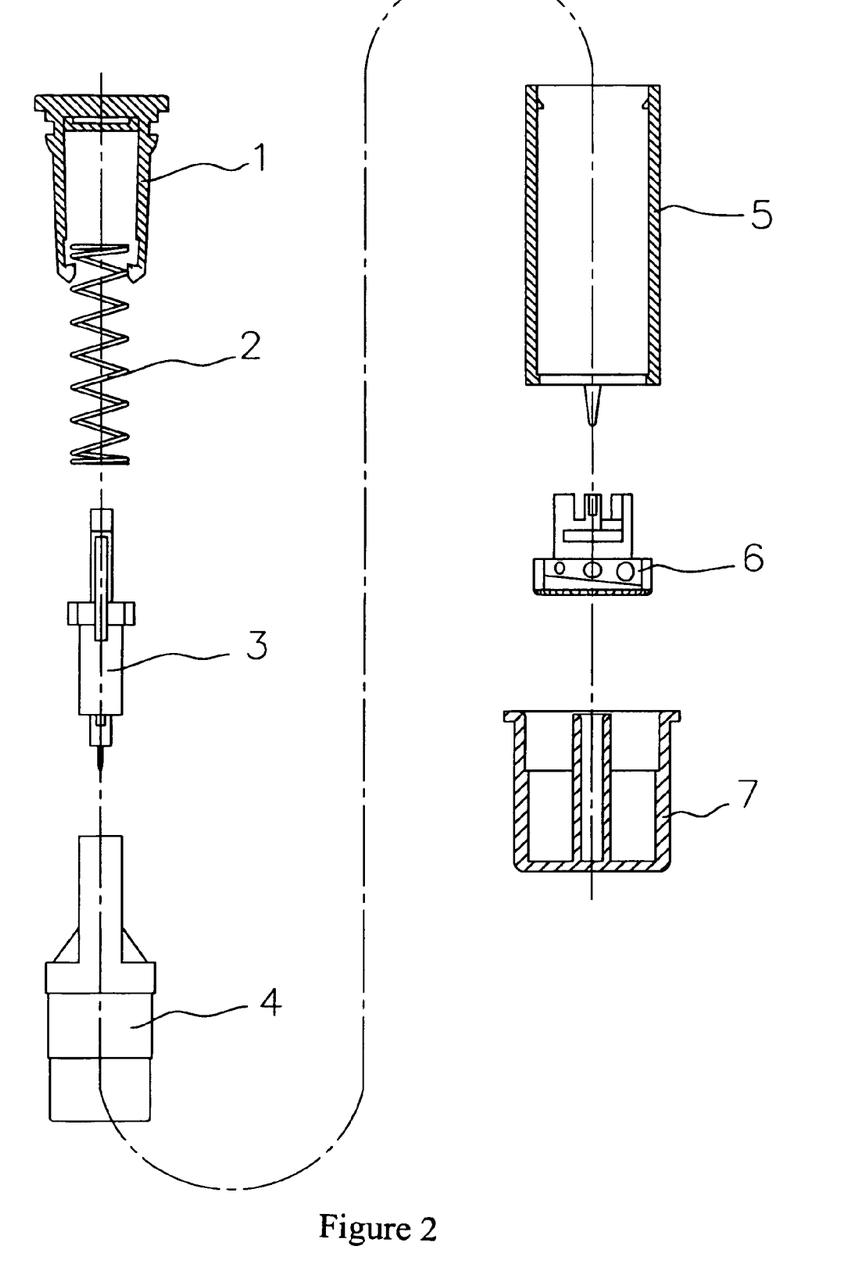
FIG. 2 is an exploded view of the embodiment.

Various embodiments will be described by the following detailed examples in connection with the accompanying drawings:

Example: as shown in FIG. 1 and FIG. 2, the safety single use (or disposable) blood taking lancet (or blood sampling needle) device with adjustable puncture depth or penetration depth may include three parts, said three parts are a needle core blast-off or release structure, adjusting head 6 adjusting the puncture depth, and nut cap 7.

Figure 3:
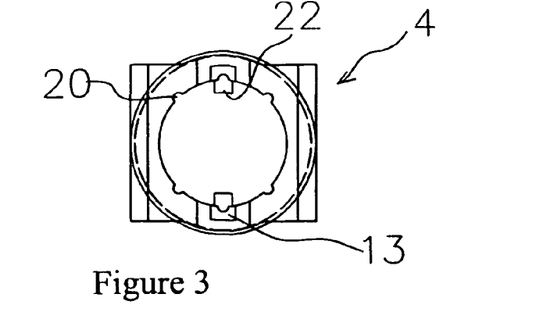
FIG. 3 is a front view of the push element of the embodiment.
Figure 4:
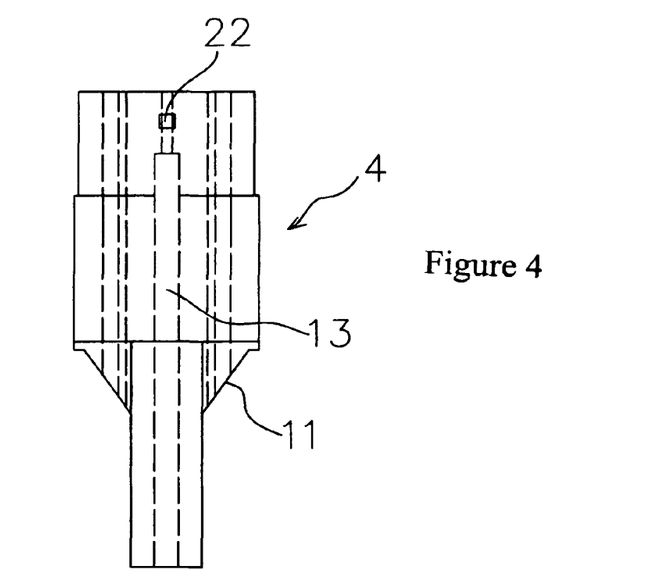
FIG. 4 is a top view of FIG. 3.
Figure 5:
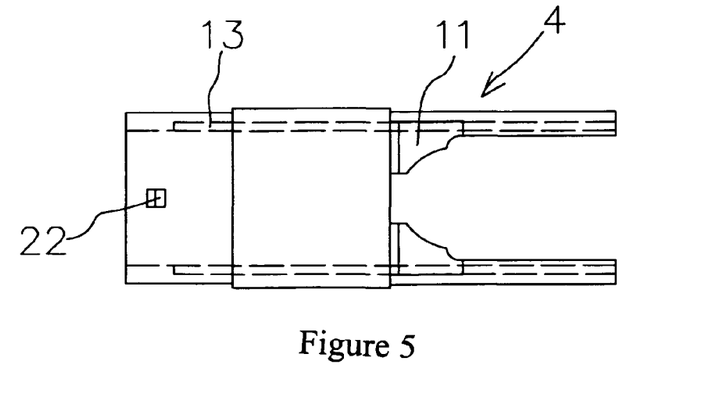
FIG. 5 is a left view of FIG. 3.
Figure 6:
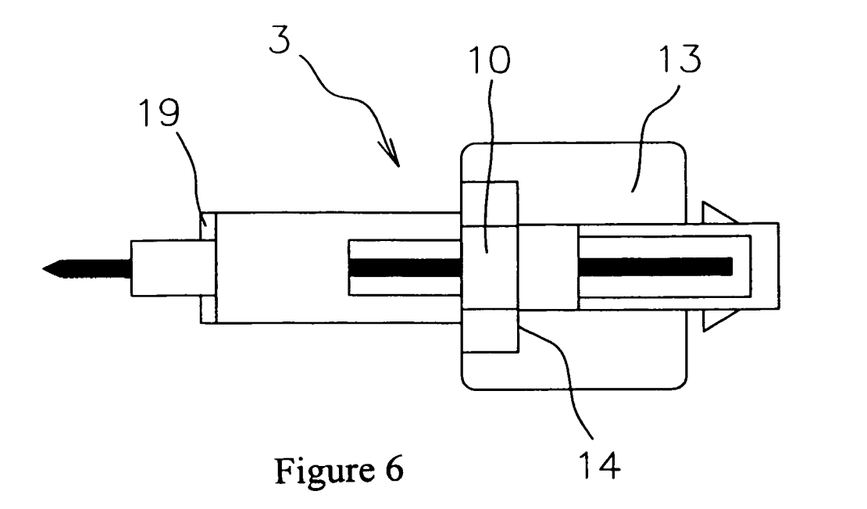
FIG. 6 is a front view of the needle core of the embodiment.
Figure 7:
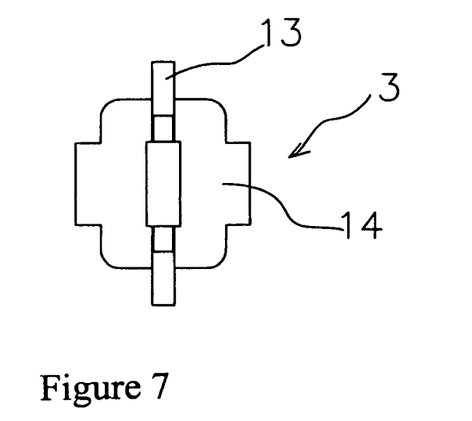
FIG. 7 is a right view of FIG. 6.
Figure 8:
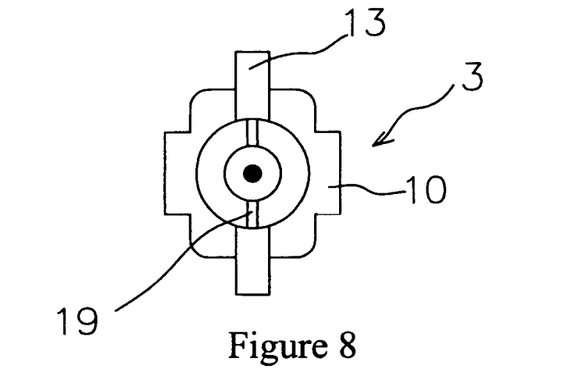
FIG. 8 is a left view of FIG. 6.
Figure 9:
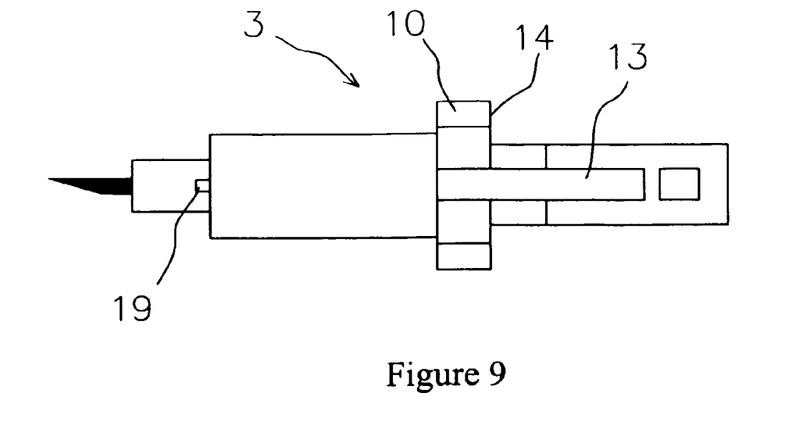
FIG. 9 is a top view of FIG. 6.

In the first part, the needle core blast-off structure may consist of a sleeve or shell 5, an end cap 1, a needle core 3 with a needle tip, a spring 2 and a push element 4. The sleeve 5 and the end cap 1 constitute a cylinder-type exterior shell. A spring clamp, or two clips, such as elastic clips 8 inside the sleeve 5 extend from end cap 1. Hooks, such as pothooks 9 mount symmetrically inward the end of the two elastic clips 8. The end cap 1 is arranged at one end of the sleeve 5. The other end of the sleeve 5 is an opening. The two elastic clips 8 on the end cap 1 are located symmetrically at inclined direction and compose converse taper structure in the vertical section plane. A barb tool 27 is located on the lateral surface of the bottom part of the elastic clips 8, as shown in FIG. 1. The barb tool 27 and a claw tool 28 located at the sleeve 5 constitute a fixed structure. In the two-dimensional presentation of FIG. 1, the sleeve 5 is preferably a rectangular sleeve structure. The thickness of the root of the two elastic clips 8 at the end cap 1 is bigger than that of the end or tip thereof. The breadth of the root matches the breadth of the sleeve 5, and thus constitutes the guide location structure of the device. The needle core 3 with a needle tip is located between the two elastic clips 8. Hook engagement elements, such as pothook engagement element or so-called "side ears" 10 are located on the needle core 3 corresponding to the hooks, such as pothooks 9, as shown in FIGS. 6-9. The side ears 10 and the pothooks 9 cooperate to form a locking structure of the needle core 3. The distance between the two pothooks 9 on the two elastic clips 8 is less than the side extending width of the two side ears 10 under free state or natural state, and a blocking face (or block off face) 14 is mounted at the top of the side ears 10. A structure which blocks the needle core 3 from returning to its initial or original position after being released from a confined state is formed between the blocking face 14 and the pothooks 9 so as to achieve a single use injection structure, as shown in FIG. 1. Two slip guide plates 12 are symmetrically mounted at two side of the needle core 3, as shown in FIGS. 6-9. The injection spring 2 is mounted between the end of the needle core 3 and the end cap 1, biasing toward the direction of injection. The side-inserted fixing slot 26 is mounted at the place corresponding to the spring 2 of the end cap 1. The base of spring 2 side-inserts into the fixing slot 26, as shown in FIG. 1. The push element 4 is mounted slidably in the opening of the other end of the sleeve 5, as shown in FIG. 1, whose front side extends from the opening. The central axis is along the injection direction (injection trace, or injection track). The push element 4 can only make axis-direction movement and cannot rotate relative to the sleeve 5. The push element inclined plane 11 (or cone plate structure), which makes the push element 4 to separate from the two sides, is mounted at the end of the push element 4 corresponding to the two elastic clips 8, as shown in FIGS. 3-5. The inclined plane 11 and the end of the two elastic clips 8 constitute a push structure. The sliding chute 13 is arranged in the inwall of the injection trace or track of the push element 4, which corresponds to the guide plates 12, as shown in FIGS. 3-5. The guide plates 12 and the sliding chute 13 cooperate to form the injection guide structure. When viewed from above, the guide structure and the lock structure are arranged as a square crossing or a cross pattern.

Figure 10:
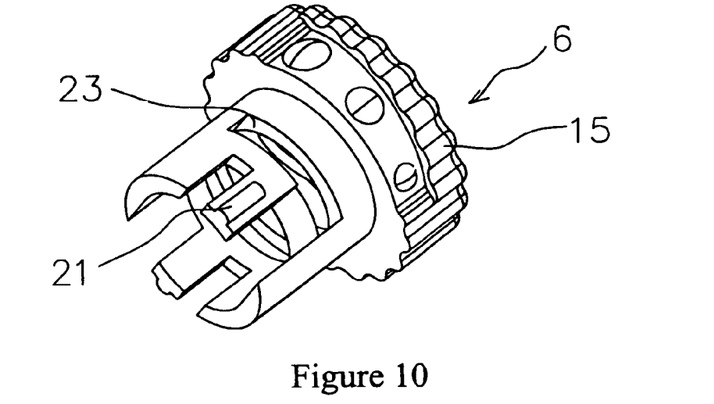
FIG. 10 is a prospective view of the adjusting head of the embodiment.
Figure 11:
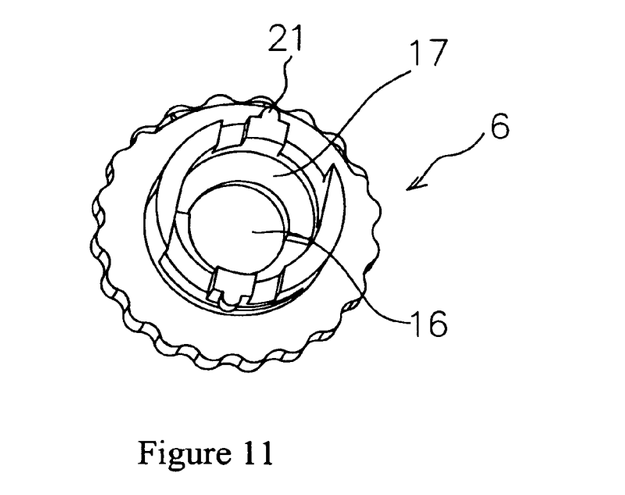
FIG. 11 is another prospective view of the adjusting head of the embodiment.
Figure 12:
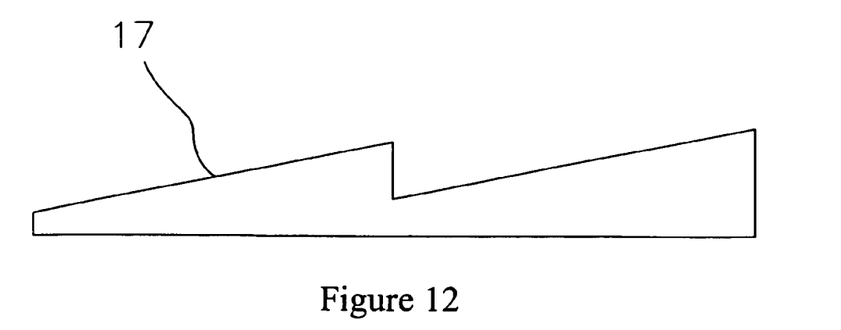
FIG. 12 is a prospective view of the revolving inclined plane of the embodiment.
Figure 13:
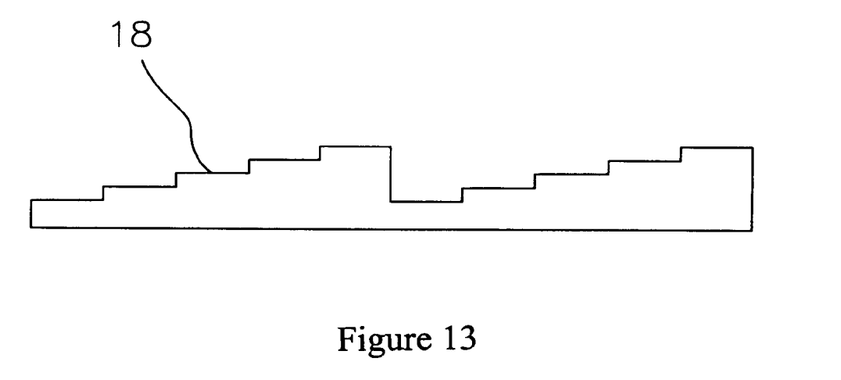
FIG. 13 is a prospective view of the revolving ladder plane of the embodiment.

The second part is shown in FIGS. 10-11. The adjusting head 6 is mounted in the head end of the push element 4, and is connected to the push element 4 rotatably. An outside face 15 which contacts the skin of a blood sampling target is mounted at the front of the adjusting head. A needle hole 16 is arranged in the centre of the outside face 15. An inside face is arranged at the back end of the needle hole 16, which faces directly to the needle core 3. The inside face may be a revolving inclined plane 17 including, for example, a helix inclined plane (see FIG. 12) or revolving ladder plane 18 including a plurality of, such as 6, revolving upstairs or downstairs steps (see FIG. 13). An impact face 19 is mounted in the head end of the needle core 3, which corresponds to the revolving inclined plane 17 or the revolving ladder plane 18. When changing the revolving angle of the adjusting head 6, the revolving inclined plane 17 or the revolving ladder plane 18 will bump into the impact face 19 of the needle core 3 at different depth of the needle hole 16. In order to make force distribution equally when the impact face 19 of needle core 3 strikes the revolving inclined plane 17 or the revolving ladder plane 18, the revolving inclined plane 17 or the revolving ladder plane 18 on the adjusting head 6 consists of a right segment and a left segment, wherein one segment coincides with the other after revolving 180° by the axial rotation. The action end of the impact face 19 of the needle core 3 is designed as a dot or a line, and corresponds to the two parts of the revolving inclined plane 17 or the revolving ladder plane 18. In order to distinguish among the different adjusting depths, a rotation orientation structure is mounted in the connection or interface between the adjusting head 6 and the push element 4. The rotation orientation structure consists of a locating slot 20 and a heave 21, which are located at the circumferential direction apart from each other. The locating slot 20 is mounted at the fitting surface of the push element 4, and the heave 21 is mounted at the fitting surface of the adjusting head 6. In one embodiment, three locating slots 20 are arranged in the circumferential direction, so as to form three kinds of adjusting puncture depth. In order to control the revolving angle of the adjusting head 6 relative to the push element 4, a corner spacing structure is mounted between the push element 4 and the adjusting head 6. The corner spacing structure consists of a projection 22 and a spacing slot, such as a spacing flat slot 23. The projection 22 is placed on the fitting surface of the push element 4, and the spacing flat slot 23 is placed on the fitting surface of the adjusting head 6. The projection 22 is located in the spacing flat slot 23, limiting the corner range by the arc length of the spacing flat slot 23.

The third part is shown in FIGS. 1-2. The nut cap 7 fits over the head end of the sleeve 5. A detecting pole 24 is mounted in the centre of the nut cap 7. A bottom hole is arranged in the head end of the detecting pole 24. An axis neck 25 is mounted in the head end of the needle core 3. The nut cap 7 is under the confined state before injection. The detecting pole 24 inserts into the needle hole 16, and cooperates with the axis neck 25 by the bottom hole.

The explanation of the above-mentioned technical solution is as follows:

1. In above-mentioned technical solution, the term "needle core" refers to the component with needle body, including needle handle and needle body on the needle handle.

2. In above-mentioned technical solution, the expression "a push element mounted slidably in the opening of the other side of the sleeve" means: on the one hand, as an inner housing, the push element is located in the outer sleeve; on the other hand, relative to the outside cover, the push element can only move along the axis direction, and cannot rotate. Otherwise, it would be impossible for the adjusting head to rotate, for example, if using a non-spherical sleeve structure.

3. In above-mentioned technical solution, the revolving planes of said adjusting head has two kinds of equivalent type, one is revolving inclined plane, the other is revolving ladder plane, wherein the revolving inclined plane consists of helix inclined plane and analogous inclined plane; the revolving ladder plane is similar to a revolving stairs structure, which has revolving upstairs or downstairs steps.

4. In above-mentioned technical solution, in order to make force distribution equally when the needle core strikes the revolving inclined plane or the revolving ladder plane, the revolving inclined plane or revolving ladder plane on the adjusting head consists of a right segment and a left segment, one segment can superposition with the other segment after revolving 180° following the axis direction; the action end of the impact face of the needle core is designed as a dot or a line, and, furthermore, corresponds to the two parts of the revolving inclined plane or revolving ladder plane.

5. In the above-mentioned technical solution, in order to distinguish the different adjusting depth, there is a revolving orientation structure in the contact surface between the push element and the adjusting head. This revolving orientation structure consists of a location slot and a heave, which is located along the circumferential direction apart from each other. Among the locating slot and the heave, one is located at the fitting surface of the push element, and the other is located at the fitting surface of the adjusting head. In other words, it is possible to locate the locating slot on the push element and locate the heave on the adjusting head; or to locate the locating slot on the adjusting head and locate the heave on the push element. The kinds relate to the number of the locating slot. For example, along the circumferential direction, there may be two to six locating slots, so as to form 2 to 6 kinds of adjusting puncture depth.

6. In above-mentioned technical solution, in order to control the revolving angle of the adjusting head relative to the push element, a corner spacing structure is mounted between the push element and the adjusting head. The corner spacing consists of a projection and a spacing flat slot. Among the projection and the spacing flat slot, one is placed on the fitting surface of the push element, and the other is placed on the fitting surface of the adjusting head. The projection is located in the spacing flat slot, limiting the corner range by the arc length of the spacing flat slot.

7. In above-mentioned technical solution, in order to determine the lock state of the needle core and the safe protection effect, a nut cap is mounted in the head end of the sleeve. The nut cap fits over the head end of the sleeve. A detecting pole is mounted in the centre of the nut cap. A bottom hole is arranged in the head end of the detecting pole. An axis neck is mounted in the head end of the needle core. The nut cap is under the confined state before injection. The detecting pole is inserted into the needle hole, therefore cooperates with the axis neck by the bottom hole.

8. In above-mentioned technical solution, in order to assemble conveniently, a side-inserted fixing slot is mounted at the place corresponding to the spring of the end cap. The base of spring is side-inserted into the fixed slot.

An exemplary operation is explained next. Before using the blood taking lancet, the two elastic clips lock the side ear of the needle core by the symmetrical pothooks. The spring being compressed, the needle core is under the state to be blasted off. During operation, after taking off the nut cap, a user may use fingers to press the sleeve and make the needle hole of the adjusting head directly into the blood taking position. At this time, the push element slides upside along the lumen or inside of the sleeve at the control of outside force. The top end inclined plane of the push element makes the end of the two elastic clips push from both sides. Then, the elastic clips detach from the side ear. The spring pushes the needle core to inject or spring along the direction guide structure. Finally, the impact face of the needle core hits the revolving inclined plane or revolving ladder plane and gets blocked (this is the utmost position of injection). The needle tip gets out of the needle hole and punctures the blood taking position. After that, the spring makes the needle core shrink back or spring back. Because of the blocking face, the needle core cannot get back to its original state before injection. Therefore, after injecting, the needle core loses the possibility or capability to inject once again. Furthermore, the needle tip hides itself in the injection cavity and does not protrude out from the needle hole. If it is needed to adjust the depth of blood taking, after taking off the nut cap, a user can turn the adjusting head. At this time, the revolving inclined plane or revolving ladder plane will make the needle tip go out of the needle hole at different depth and will face the impact face of the needle. Therefore, the user can get different puncture depth by changing the outer length of the needle injection. Furthermore, the user can get different kinds of positions by turning the orientation structure, making the adjustment of rotation intermittently or one step at a time. Also, grating sound may be produced to enable the user to handle the depth adjustment more easily and more precisely.

Because of the application the above-mentioned technical solution, compared with the prior art, the present embodiment has the following advantages:

1. There is only relative rotation between the adjusting head and the push element, with no relative axial movement therebetween. Thus, the accuracy and the consistence of each kind is controlled by the revolving plane and the angle location. Therefore, this mutual cooperation results in less error, which could increase the accuracy of puncture depth.

2. The adjusting head uses a mode that is better than the traditional mode of helix machine. It decreases the axis direction movement between each component, which is propitious to simplify the structure and decrease the volume and the length.

3. The needle core and the push element connect with the guide plate by the two sides sliding chute, which makes the injection direction guide of the needle core much better, the injection more reliable and more pleasant to feel. In comparison, the injection direction guide of the prior art is disadvantaged.

4. There is a blocking face on the top side of the side ear in the needle core. After injection, this blocking face can cooperate with the bottom of the pothooks to form a structure, which can block needle core from returning to its original position, between the blocking face and the symmetrical pothooks, so as to ensure that the needle core would not go back to lock state after needle core injection, thus avoiding the possibility to inject again, achieving a real single use injection structure.

5. There is a detecting pole in the nut cap model. The detecting pole can be used to test the lock state of the needle core. When the nut cap is installed, if a user finds that the position of nut cap is not right or cannot be installed before using it, the user can tell and conclude that the needle core is under the state of after injection. Thus, the detecting pole can not only protect the needle, but can also be used to examine the structure.

6. There are two symmetrical clips on the end cap. This makes the hooks of the end of the clips have certain holding force in locking the needle core, which further enhances the reliability of locking, and thus ensures the device to stay in a locking state In conclusion, from an optimum design view point, the instrument of the disclosed embodiment combines an adjusting head structure and a blast-off structure, which increases performances on assembly structure, reliability, safety, adjustable ability and hand feeling of injection of the product, especially on the integrate performance.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A safety single use blood taking lancet, having a puncture depth that is adjustable, including a needle core blast-off structure and an adjusting head with adjustable puncture depth, wherein:
    said needle core blast-off structure comprises:
    a sleeve and an end cap at one end of the sleeve composing a cylinder-type outer shell, two elastic clips inside the sleeve extending from the end cap, pothooks mounted symmetrically inward an end of the two elastic clips, the other end of the sleeve being an opening;
    a needle core with a needle tip mounted between the two elastic clips, side ears mounted on the needle core corresponding to the pothooks, the side ears and the pothooks cooperating to form a locking structure of the needle core; a distance between the two pothooks on the two elastic clips being less than a side extending width of the two side ears under free state, and a blocking face mounted at a top of the side ears, a structure which blocks the needle core from returning to an initial position after being released in an injection being formed between the blocking face and the pothooks so as to achieve a single use injection structure; two slip guide plates symmetrically mounted at two side of the needle core;
    an injection spring mounted between an end of the needle core and the end cap, and biased toward a direction of injection;
    a push element mounted slidably in the opening of the other end of the sleeve, whose front side extending from the opening, a central axis being along the injection direction; a push element inclined plane or a cone plane structure, which makes the two elastic clips to separate from two sides, mounted at an end of the push element corresponding to the two elastic clips, the inclined plane and the end of the two elastic clips composing a push structure; a sliding chute mounted in an inwall of an injection trace of the push element, which corresponds to the guide plates, the guide plates and the sliding chute cooperating to form an injection guide structure; when viewed from above, the guide structure and the lock structure being arranged as a square crossing;
    said adjusting head being mounted in the head end of the push element, which connects with the push element rotatably, an outside face which contacts the skin of an injection object being mounted at the front of the adjusting head, a needle hole being located in a centre of the outside face, an inside face of the adjusting head being arranged in a back end of the needle hole, which faces directly to the needle core, said inside face being a revolving ladder plane that is an integral part of the adjusting head and that extends radially inwardly from an interior surface of the adjusting head, an impact face being mounted in the head end of the needle core, which corresponds to the revolving ladder plane, when changing a revolving angle of the adjusting head, the revolving ladder plane bumping into the impact face of the needle core at different depth of the needle hole, wherein the adjusting head only rotationally moves relative to the push element without moving in an axial direction of the central axis relative to the push element.

2. The safety blood taking lancet of claim 1, wherein the revolving ladder plane on said adjusting head consists of a right segment and a left segment, wherein one segment coincides with the other after revolving 180° relative to a rotation axis, an action end of the impact face of the needle core being designed as a dot or a line, and corresponding to two parts of the revolving ladder plane.

3. The safety blood taking lancet of claim 1, wherein a rotation orientation structure is mounted in a revolving connection between the adjusting head and the push element, said rotation orientation structure consisting of a locating slot and a heave, which are located in a circumferential direction apart from each other, one of the locating slot and the heave being mounted at a fitting surface of the push element, and the other being mounted at a fitting surface of the adjusting head.

4. The safety blood taking lancet of claim 3, wherein two to six locating slots are arranged in the circumferential direction, so as to form two to six kinds of adjusting puncture depth.

5. The safety blood taking lancet of claim 1, wherein a corner spacing structure is mounted in the adjusting head corresponding to the push element, said corner spacing structure consisting of a projection and a spacing flat slot, one of the projection and the spacing flat slot being mounted on a fitting surface of the push element, and the other being mounted on a fitting surface of the adjusting head, the projection being mounted in the spacing flat slot, limiting a corner range by an arc length of the spacing flat slot.

6. The safety blood taking lancet of claim 1, wherein a nut cap is mounted in the head end of the sleeve, said nut cap fitting over the head end of the sleeve, a detecting pole being mounted in a centre of the nut cap, a bottom hole being arranged in the head end of the detecting pole, an axis neck being mounted in the head end of the needle core, the nut cap being under a confined state before injection, the detecting pole being inserted into the needle hole and cooperating with the axis neck by the bottom hole.

7. The safety blood taking lancet of claim 1, wherein a side-inserted fixing slot is mounted at a location corresponding to the spring of the end cap, a base of the spring side being side-inserted into the fixing slot.

8. The safety blood taking lancet of claim 2, wherein a rotation orientation structure is mounted in a revolving connection interface between the adjusting head and the push element, said rotation orientation structure consisting of a locating slot and a heave, which are located in a circumferential direction apart from each other, one of the locating slot and the heave being mounted at a fitting surface of the push element, and the other being mounted at a fitting surface of the adjusting head.

9. The safety blood taking lancet of claim 8, wherein two to six locating slots are arranged in the circumferential direction, so as to form two to six kinds of adjusting puncture depth.

10. The safety blood taking lancet of claim 2, wherein a corner spacing structure is mounted in the adjusting head corresponding to the push element, said corner spacing structure consisting of a projection and a spacing flat slot, one of the projection and a spacing flat slot being mounted on a fitting surface of the push element, and the other being mounted on a fitting surface of the adjusting head, the projection being mounted in the spacing flat slot, limiting a corner range by an arc length of the spacing flat slot.

\* \* \* \* \*